US012797570B2

(12) United States Patent
Katz et al.

(10) Patent No.: US 12,797,570 B2
(45) Date of Patent: Nov. 17, 2026

(54) OXYGEN TUBING AFFIXING DEVICE

(71) Applicant: INTERNATIONAL BUSINESS MACHINES CORPORATION, Armonk, NY (US)

(72) Inventors: Jessica Katz, Brooklyn, NY (US); Tyler Nicole King, Durham, NC (US)

(73) Assignee: International Business Machines Corporation, Armonk, NY (US)

( * ) Notice: Subject to any disclaimer, the term of this patent is extended or adjusted under 35 U.S.C. 154(b) by 968 days.

(21) Appl. No.: 17/934,643

(22) Filed: Sep. 23, 2022

(65) Prior Publication Data

US 2024/0100283 A1 Mar. 28, 2024

(51) Int. Cl.
*A61M 16/06* (2006.01)
*A61M 16/00* (2006.01)

(52) U.S. Cl.
CPC .... *A61M 16/0683* (2013.01); *A61M 16/0003* (2014.02); *A61M 16/0051* (2013.01); *A61M 16/0672* (2014.02); *A61M 2205/13* (2013.01); *A61M 2205/18* (2013.01); *A61M 2209/088* (2013.01); *A61M 2230/205* (2013.01)

(58) Field of Classification Search
None
See application file for complete search history.

(56) References Cited

U.S. PATENT DOCUMENTS

| | | | | |
|---|---|---|---|---|
| 5,025,805 A * | 6/1991 | Nutter | A61M 16/0666 128/207.18 |
| 5,551,423 A * | 9/1996 | Sugiura | A61B 5/6816 600/323 |
| 6,026,811 A * | 2/2000 | Settle | A61M 16/0666 128/207.18 |
| 7,658,716 B2 | 2/2010 | Banet | |
| 8,229,532 B2 | 7/2012 | Davis | |
| 2004/0139973 A1* | 7/2004 | Wright | A61M 16/0672 128/207.18 |
| 2005/0038453 A1* | 2/2005 | Raulerson | A61M 25/02 606/151 |
| 2008/0154098 A1 | 6/2008 | Morris | |
| 2008/0190436 A1* | 8/2008 | Jaffe | A61M 16/0688 128/207.18 |

(Continued)

FOREIGN PATENT DOCUMENTS

| | | |
|---|---|---|
| CN | 111317899 A | 6/2020 |
| KR | 102071684 B1 | 1/2020 |
| NZ | 756942 A | 5/2020 |

OTHER PUBLICATIONS

Anonymous. "BCI 3301 Hand Held Pulse Oximeter With 3078 Ear Sensor." Accessed Jul. 20, 2022. 10 pages. Published by Turner Medical. https://www.turnermedical.com/BCI_3301_HAND_HELD_PULSE_OXIMETER_WITH_3078_EAR_SE_p/bci_3301a3_ear.htm.

(Continued)

*Primary Examiner* — Timothy A Stanis
*Assistant Examiner* — Thomas Z Chang
(74) *Attorney, Agent, or Firm* — Seed Intellectual Property Law Group LLP

(57) ABSTRACT

A flexible ear cuff, configured to receive an oxygen tube and the flexible ear cuff is shaped to nestle between a pinna of an ear and a head of a patient. Thus, the flexible ear cuff may be used to secure the oxygen tube to the head of a patient.

18 Claims, 6 Drawing Sheets

(56) References Cited

U.S. PATENT DOCUMENTS

| | | | | |
|---|---|---|---|---|
| 2011/0203595 | A1* | 8/2011 | Hashemieh ....... | A61M 16/0672 128/207.18 |
| 2013/0146064 | A1* | 6/2013 | Dryden ................ | A61M 15/08 128/207.18 |
| 2017/0065785 | A1* | 3/2017 | Roberts ............. | A61M 16/0683 |
| 2018/0001045 | A1* | 1/2018 | Cortez, Jr. ............ | A61M 16/14 |
| 2019/0076100 | A1* | 3/2019 | Narkiss ................. | A61M 16/06 |
| 2019/0183359 | A1 | 6/2019 | Weebadde | |
| 2019/0254565 | A1 | 8/2019 | Toth | |
| 2021/0283357 | A1* | 9/2021 | Leonard ............ | A61M 16/1005 |
| 2021/0330259 | A1 | 10/2021 | Liu | |
| 2022/0054786 | A1* | 2/2022 | Huss ................. | A61M 16/1045 |

OTHER PUBLICATIONS

Anonymous. "Epic Air Sport ANC True Wireless Earbuds." Accessed Jul. 20, 2022. 16 pages. Published by JLab. https://www.jlab.com/products/epic-air-sport-anc-true-wireless-earbuds?variant=34694359482440&currency=USD&utm_medium=product_sync&utm_source=google&utm_content=sag_organic&utm_campaign=sag_organic&utm_source=google&utm_medium=shopping&utm_campaign=13759308923&utm_content=124901559512&utm_term=pla-1364476863485&gclid=CjwKCAjwwsmLBhACEiwANq.

Anonymous. "OxiWear—A Sleek Pulse Ox Ear-Wearable." Accessed Jul. 20, 2022. 4 pages. Published by IndieGoGo. https://www.indiegogo.com/projects/oxiwear-a-sleek-pulse-ox-ear-wearable#/.

Anonymous. "TMD2636 IR Proximity Detection Module." Accessed Jul. 20, 2022. 3 pages. Published by AMS. https://ams.com/TMD2636.

Davies, et al., "In-Ear SpO2: A Tool for Wearable, Unobtrusive Monitoring of Core Blood Oxygen Saturation." Published Aug. 28, 2020. 12 pages. Published by MDPI. In Sensors 2020, 20(17), 4879. https://doi.org/10.3390/s20174879.

Rafanelli, A., "Fewer Intubations, More At-Home Care: Covid-19 Is Changing Doctors' Approach to Oxygen Therapy." Published Mar. 11, 2021 by Direct Relief. 9 pages. https://www.directrelief.org/2021/03/fewer-intubations-more-at-home-care-covid-19-is-changing-doctors-approach-to-oxygen-therapy/.

* cited by examiner

OXYGEN TUBING AFFIXING DEVICE

BACKGROUND

Aspects of the present disclosure relate to an oxygen tubing affixing device.

Some people with breathing disorders can't get enough oxygen naturally. They may need supplemental oxygen, or oxygen therapy. People who receive oxygen therapy often see improved energy levels and sleep, and better quality of life.

To determine whether a person will benefit from oxygen therapy, doctors test the amount of oxygen in their arterial blood. Another way to check is using a pulse oximeter that indirectly measures oxygen levels, or saturation, without requiring a blood sample. The pulse oximeter clips onto a person's body part, like a finger. Low levels mean that a person may be a good candidate for supplemental oxygen.

Normal levels of arterial blood oxygen are between 75 and 100 mmHg (millimeters of mercury). An oxygen level of 60 mmHg or lower indicates the need for supplemental oxygen.

BRIEF SUMMARY

The present disclosure provides a device, system, and method for an oxygen tubing affixing device. In some embodiments, the device includes a flexible ear cuff configured to receive an oxygen tube, wherein the ear cuff is shaped to nestle between a pinna of an ear and a head of a patient; and a proximity sensor configured to fit around the oxygen tube and issue an alert when a distance between the head of the patient and the proximity sensor breaches a threshold.

In some embodiments, the system includes a flexible ear cuff configured to receive an oxygen tube, wherein the ear cuff is shaped to nestle between a pinna of an ear and a head of a patient.

In some embodiments, the method includes attaching a flexible ear cuff over an oxygen tube, wherein the ear cuff nestled between a pinna of an ear and a head of a patient.

DETAILED DESCRIPTION

Aspects of the present disclosure relate an oxygen tubing affixing device. While the present disclosure is not necessarily limited to such applications, various aspects of the disclosure may be appreciated through a discussion of various examples using this context.

Patients who rely on oxygen may struggle with keeping their oxygen tubes secure in their noses. Due to the oxygen tubing cylinder shape, with movement, the tube has a tendency to slip off of the patient's ear which pulls the oxygen nose piece either out of their nose or distorts it in a way that prevents them from receiving the necessary level of oxygen they need. There isn't a system in place to let doctors or nurses know when oxygen levels are low due to equipment malfunction. Because of this, patients who are unable to help themselves when a problem arises might be at risk for dangerously low oxygen levels and create a healthcare professional. As the technology evolves, the need to monitor pulse oximeter saturation is increasingly vital.

Therefore, in some embodiments, a device and a system are proposed to securely affix a patient's oxygen tubing in place, monitor blood oxygen levels, and/or alert healthcare staff when the tubing slips away from the face.

In some embodiments, an ear attachment device combines an earlobe oximeter clamp housing and over-the-ear-cuff protector to securely attach oxygen tubes to a patient's head. This design combines the oxygen tube and oximeter into a single device. In some embodiments, an attached sensors alerts doctors and nurses when a patient's tube has slipped out of place. This device improves efficiency of hospital staffing, and ultimately improves patient care.

Oxygen and Pulse Oximeters are in high demand due to the value associated with their use inpatient recovery in hospitals, hospice, and post-hospital care. However, the use of oxygen tubes and pulse oximeters can create issues. Oxygen tubes and pulse oximeters may often come detached and/or create irritation around a patient's head. In some embodiments, the proposed ear attachment device secures the oxygen tubing and pulse oximeter to a patient's head with an attachment sensor that gives an alert when the oxygen tubing becomes detached.

Figure 1:
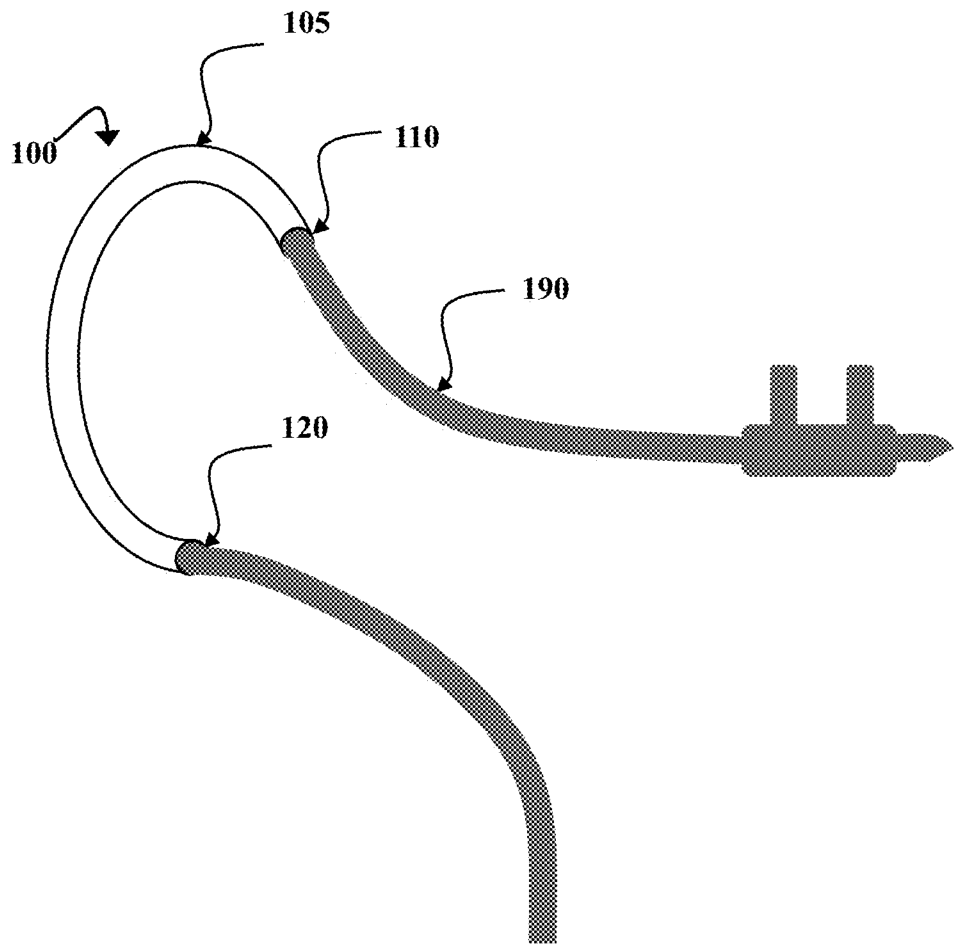
FIG. 1 depicts a device comprised of a flexible ear cuff according to various embodiments of the present disclosure.

FIG. 1 depicts an example device 100 comprised of a flexible ear cuff 105 with a first end 120 and a second end 110. In some embodiment, the ear cuff 105 is designed with a hollow casing to house and secure a patient's oxygen tubing 190. In some embodiment, the flexible ear cuff 105 may be composed of a flexible material such as rubber, silicone, latex, nitrile, or some other flexible material. Different materials may be selected based on patient allergies. In some embodiments, flexible ear cuff 105 is designed to slip over oxygen tubing 190. For example, the flexible ear cuff 105 may be designed to slide over oxygen tubing 190. In some embodiments, the ear cuff 105 may have a slit running its length from first end 120 to second end 110 to allow the flexible ear cuff to be applied to the oxygen tubing 190 without sliding over the entire oxygen tubing 190.

Figure 2:
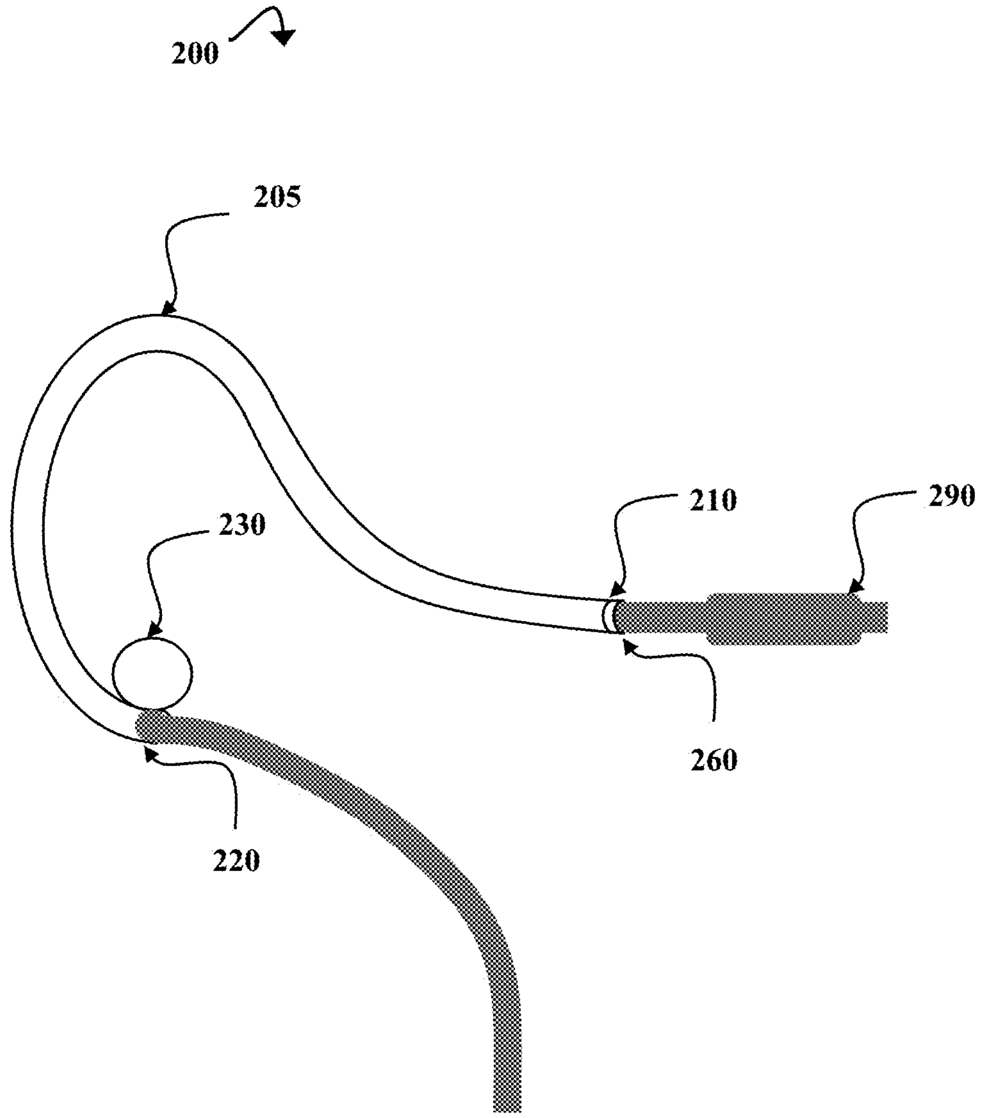
FIG. 2 depicts a device comprised of a flexible ear cuff, an attached pulse oximeter earlobe clamp, and an attached attachment sensor according to various embodiments of the present disclosure.

FIG. 2 depicts a device 200 comprised of a flexible ear cuff 205 with a first end 220 and a second end 210, an attached pulse oximeter earlobe clamp 230 and an attachment sensor 260. In some embodiment, the flexible ear cuff 205 may be composed of a flexible material such as rubber, silicone, latex, nitrile, or some other flexible material. Different materials may be selected based on patient allergies. In some embodiments, flexible ear cuff 205 is designed to slip over oxygen tubing 290. For example, the flexible ear cuff 205 may be designed to slide over oxygen tubing 290. In some embodiments, the ear cuff 205 may have a slit running its length form first end 220 to second end 210 (not depicted) to allow the flexible ear cuff 205 to be applied to oxygen tubing 290 without sliding over the entire tubing 290. In some embodiments, bottom of the flexible ear cuff

205 has an earlobe clamp 230 that both aids in further securing the device 200 to the patient's ear and measures a patient's blood oxygen levels. In some embodiments, device 200 includes sensors that detect when the patient's oxygen tubing 290 has become separated from the patient's face or nose.

In some embodiments, device 200 is a flexible piece designed to securely fasten behind a patient's ear. In some embodiments, the device is hollow, allowing for a patient's oxygen tubing cylinder 290 to be fed through ear cuff 205. The ear cuff 205 is designed to conform to the shape of the ear, and acts as a casing to ensure the patient's oxygen tubing cylinder does not slip from their face. In addition to keeping the oxygen tubing cylinder 290 in place on the patient's face, device 200 is equipped with sensor(s) 260 at or near second end 210 to detect if the oxygen tubing cylinder 290 has been displaced.

In some embodiments, the ear cuff 205 is constructed of medical-grade silicone rubber (or a like material), which is flexible and durable. Silicone has a high coefficient of friction and inherent surface tack, which increases the friction of the tubing 290 and reduces the possibility of slippage.

At the base of the ear cuff 205 near end 220 is a wireless pulse oximeter earlobe clamp 230 (referred to as the pulse oximeter) which, when affixed to a patient's earlobe, monitors blood oxygen levels. Additionally, the pulse oximeter 230 aids in further securing the oxygen tubing cylinder 290 to the patient. In some embodiments, the pulse oximeter 230 may include wireless (e.g., Bluetooth) connectivity to provide flexibility in alerting capabilities.

Device 200 monitors the status of a patient's oxygen tubing cylinder 290 and collects a patient's blood oxygen vitals. In some embodiments, sensor 260 may detect if the oxygen tubing cylinder has slipped out of place, while pulse oximeter 230 monitors blood oxygen vitals. In some embodiments, if an abnormality occurs—due, for example, to a tubing 290 slip or a drop in blood oxygen levels—the device 200 issues an alert.

In some embodiments, in a healthcare facility setting, the device 200 can connect to the facility's central nursing station and the patient's bedside monitor via a wireless technique (e.g., Bluetooth). In some embodiments, the device 200 can also be connected to a patient's hospital wristband to be paired with the patient's assigned hospital code. In some embodiments, device 200 can connect to a mobile app of a designated caregiver. For example, device 200 may connect to a mobile device being monitored by a patient's health care professional.

In some embodiments, the device issues an alert to care staff through the paired devices (e.g., central station, bedside monitor, etc.) if a patient's conditions and vitals become dangerous. In some embodiments, because of changing goals in pulse oxygen saturation (e.g., the measurement for the amount of oxygen in a patients blood) for patients, the threshold of "dangerous" is pre-determined by users (e.g., medical professionals) during device configuration and may be adjusted by users in an administrative setting on a patient-by-patient basis. To prevent false alarms, the device may have a delay (e.g., 60 seconds) before registering anomalous events as dangerous and worthy of an alert. In some embodiments, this 60-second wait time is the device default, but can be overridden by the user during device configuration or any time during the device's lifetime. In some embodiments, thresholds can also be defined on a patient-by-patient basis.

In some embodiments, device 200 can be scanned with a registration mark (such as a bar code, not depicted) and tied to the patient's hospital wristband and electronic health records. In some embodiments, an individual patient profile may be linked to device 200 and may be used by care staff. In some embodiments, the profile helps provide context to doctors in an ever-changing hospital setting. The profile may also aid in patient hand-off while moving from a hospital to hospice care, or from a hospital to at-home care. For example, if John moves from a hospital into hospice care, his profile may be used at any facility he is transferred to providing additional data to his new healthcare staff so they can personalize his care experience.

In some embodiments, the device can further support patients' aftercare in hospice facilities, at home, and even with virtual nurses through telemedicine. In some embodiments, device 200 may support caretakers and alerts them when a patient reaches low oxygen levels and can document trends to inform decisions made by caretakers.

In some embodiments, when a patient's ear cuff is removed or replaced in a hospital setting, its replacement is re-paired with the associated devices via a wireless connection by a healthcare practitioner and paired with the patient's associated hospital code (e.g., with the patient's hospital wristband) and electronic health records.

In some embodiments, if device 200 is removed or replaced in an at-home setting, the paired mobile application allows a caregiver to note a device swap, so no abnormalities are recorded during the time of the swap. For example, a replacement device is re-paired with the app and the patient's profile via wireless connection.

In some embodiments, device 200 is able to connect to a healthcare facility's central station to alert staff to issues related to a patient's blood oxygen. Additionally, in some embodiments, device 200 can be connected to a mobile or desktop application with the option to connect with a patient's electronic health records to track and record patient vitals and blood oxygen levels. Beyond the hospital, the device can further support patients' aftercare in hospice facilities or at home.

Figure 3A:
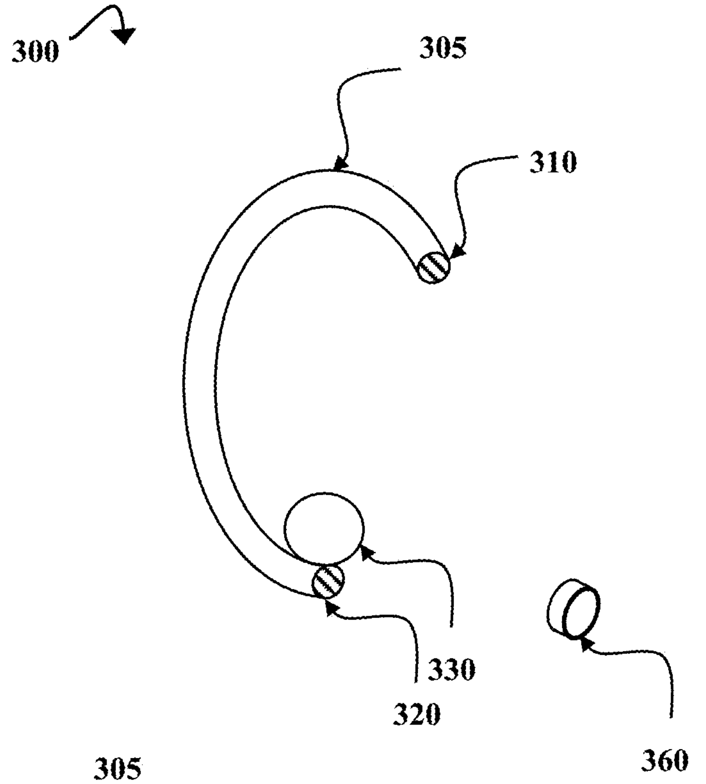
FIGS. 3A, 3B, and 3C depict a device comprised of a flexible ear cuff, an attached pulse oximeter earlobe clamp, and an attached attachment sensor according to various embodiments of the present disclosure.
Figure 3B:
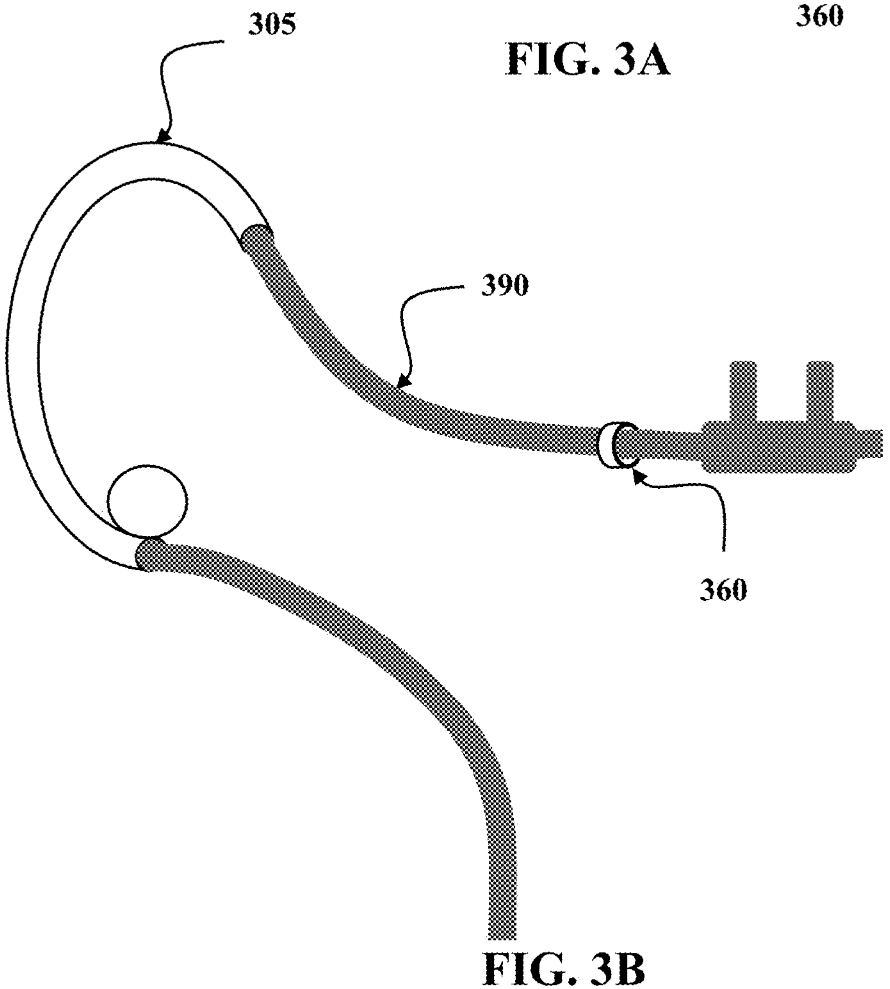
Figure 3C:
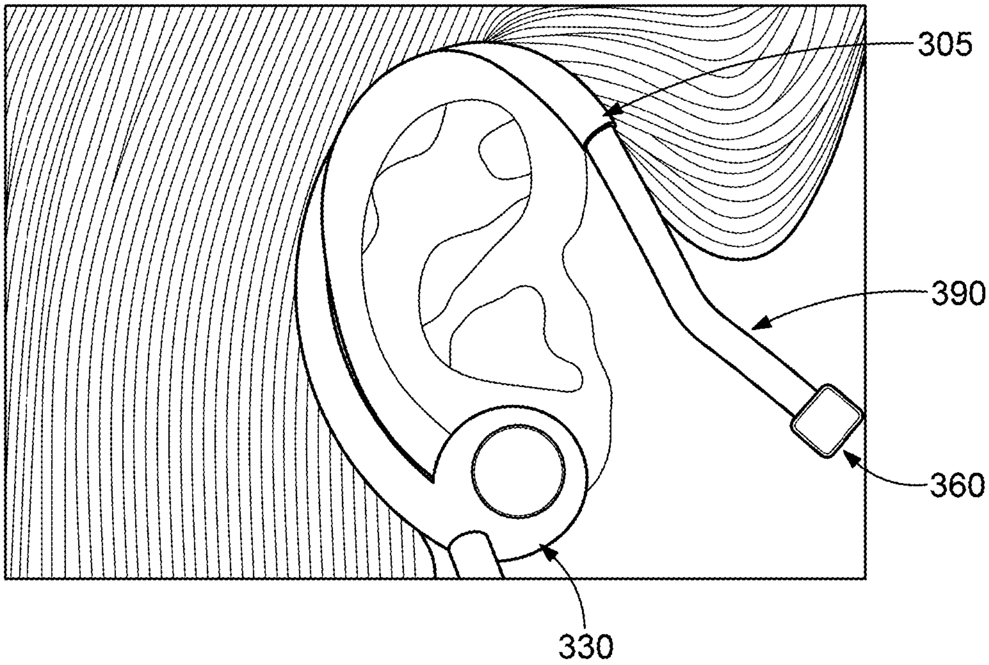

FIGS. 3A, 3B, and 3C depict a device 300 (similar to device 200 depicted in FIG. 2) comprised of a flexible ear cuff 305 with a first end 320 and a second end 310, an attached pulse oximeter earlobe clamp 330 and an attached attachment sensor 360. In some embodiments, attachment sensor 360 is not attached to flexible ear cuff 305 and may be positioned along oxygen tubing 390. For example, since the part of oxygen tubing 390 that is connected to the nose is the most vital attachment point, attachment sensor 360 may be positioned near the portion of oxygen tubing 390 that will connect to the nose. Example variations of attachment sensor 360 are depicted in FIGS. 4A and 4B.

Figure 4A:
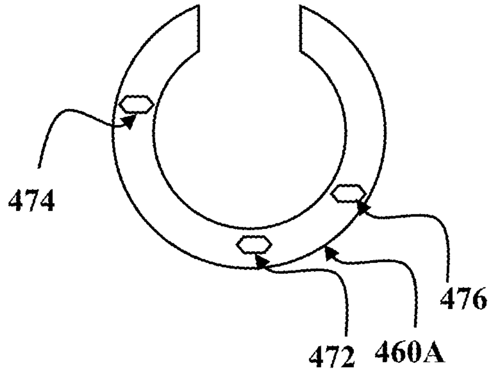
FIGS. 4A and 4B depict some example variants of attachment sensor according to various embodiments of the present invention.
Figure 4B:
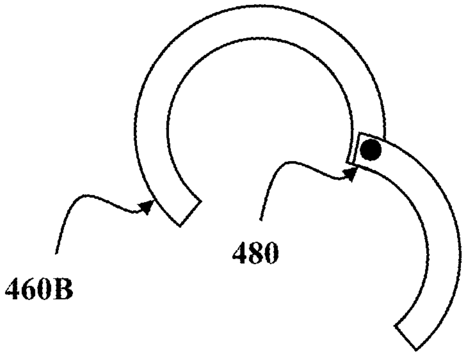

FIGS. 4A and 4B depict some example variants of attachment sensor 360 or sensor 260. In some embodiments, attachment sensor 460A has a gap allowing attachment sensor 460A to slip around an oxygen tube.

In some embodiments, attachment sensor 460B has two parts to be closed around an oxygen tube. In some embodiments, the parts of attachment sensor 460B are connected with hinge 480. In some embodiments, the attachment sensors 460A and/or 460B have a wireless connection component 474 (e.g., Bluetooth), a proximity sensor 472, and a micro controller 476. In some embodiments, attachment sensors 460A and/or 460B comprise a medical-grade polymer body (e.g., polypropylene) encased in medical-grade silicone rubber. In some embodiments, wireless connection component 474 (e.g., Bluetooth) and proximity sensor 472 are connected to micro controller 476. In some embodiments, a proximity sensor is a sensor configured to detect the presence of a human in close proximity without any physical contact. Some examples of sensors that may be used include capacitive, capacitive displacement sensor, optical, photoelectric, photocell (reflective), laser rangefinder, passive (such as charge-coupled devices), passive thermal infrared, radar, reflection of ionizing radiation, sonar (e.g., active or passive), ultrasonic sensor, fiber optics sensor, and hall effect sensor.

Figure 5:
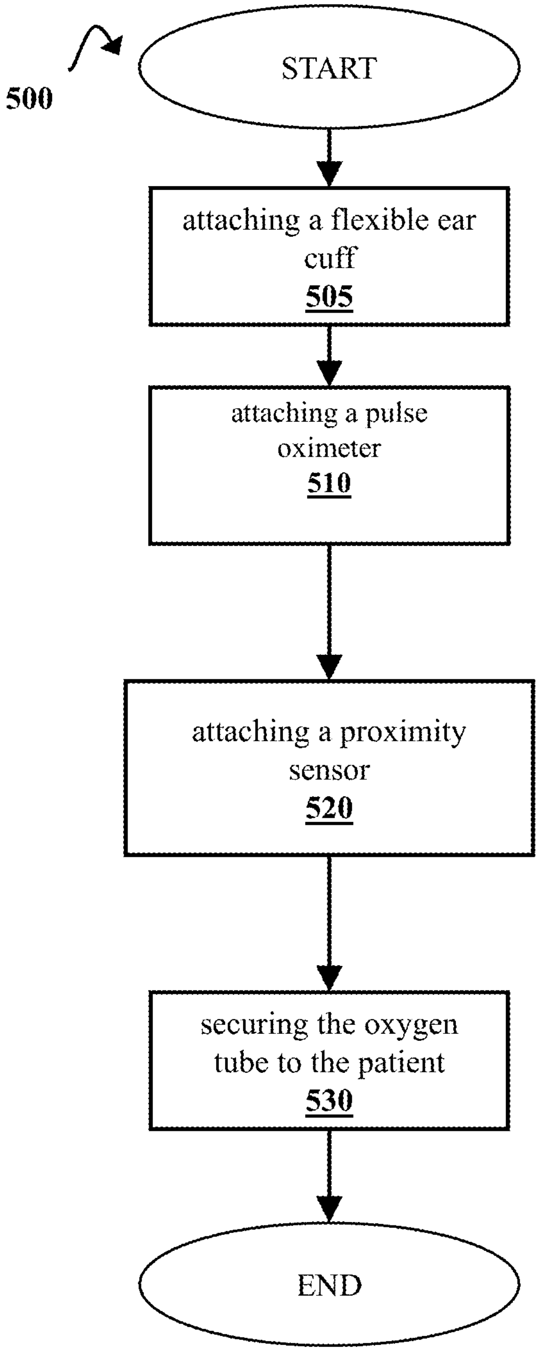
FIG. 5 an example method 500 for securing oxygen tubing to a patient according to various embodiments of the present disclosure.

FIG. 5 depicts an example method 500 for securing oxygen tubing to a patient. Operations of method 500 may be enacted the devices described in above.

Method 500 begins with operation 505 where a flexible ear cuff configured to receive an oxygen tube is attached to a patient. In some embodiments, the ear cuff is shaped to nestle between a pinna of an ear and a head of a patient. In some instances, the anatomy of the external ear is known as the auricle or pinna and includes the earlobe. In some embodiments, the flexible ear cuff is a tube with an inner diameter that is larger than the outer diameter of the oxygen tubing. For example, the flexible ear cuff may be sized so it can be slid over an oxygen tube.

Method 500 continues with operation 510 where a pulse oximeter is attached, with an earlobe clamp, at a first end of the flexible ear cuff, to an earlobe of the patient. In some embodiments, the flexible ear cuff may comprise a sleeve that a pulse oximeter may fit into. For example, a silicone flexible ear cuff may have a sleeve that a commercially available pulse oximeter may fit into.

At operation 520, a proximity sensor is attached to the oxygen tube. In some embodiments, the proximity sensor may be attached to the flexible ear cuff (as in FIG. 2) or separate from the ear cuff (as in FIG. 3A). In some embodiments, the attachment sensor has two pieces connected by a hinge, and the two pieces are configured to close around the oxygen tube and secure the attachment sensor to the oxygen tube (as depicted in FIG. 4A).

In operation 530 the oxygen tube is secured to the patient in such a manner that the proximity sensor is within a threshold proximity to the patient's skin. In some embodiments, the proximity sensor may continually or intermittently determine if it is within a proximity of the patient's skin. For example, the proximity sensor may include an infrared sensor, and the reading on the infrared sensor falling below a threshold may indicate that the sensor has moved away from the skin of the patient. In some embodiments, upon a determination that the proximity sensor is not within range of the skin, the system may send an alert to a caregiver.

The flowchart and block diagram in FIG. 5 illustrate the architecture, functionality, and operation of possible implementations of systems, methods, and computer program products according to various embodiments of the present invention. In this regard, each block in the flowchart or block diagram may represent a module, segment, or portion of instructions, which comprises one or more executable instructions for implementing the specified logical function (s). In some alternative implementations, the functions noted in the blocks may occur out of the order noted in FIG. 5. For example, two blocks shown in succession may, in fact, be executed substantially concurrently, or the blocks may sometimes be executed in the reverse order, depending upon the functionality involved. It will also be noted that each block of the block diagram and/or flowchart illustration, and combinations of blocks in the block diagram and/or flowchart illustration, can be implemented by special purpose hardware-based systems that perform the specified functions or acts or carry out combinations of special purpose hardware and computer instructions.

The descriptions of the various embodiments of the present disclosure have been presented for purposes of illustration but are not intended to be exhaustive or limited to the embodiments disclosed. Many modifications and variations will be apparent to those of ordinary skill in the art without departing from the scope and spirit of the described embodiments. The terminology used herein was chosen to explain the principles of the embodiments, the practical application or technical improvement over technologies found in the marketplace, or to enable others of ordinary skill in the art to understand the embodiments disclosed herein.

What is claimed is:

1. A device comprising:

a flexible ear cuff with a first end and a second end, the first end comprising a sleeve configured to receive a pulse oximeter and the second end configured to receive an oxygen tube, wherein the pulse oximeter is fitted into the sleeve, wherein the flexible ear cuff is configured to support the pulse oximeter that monitors blood oxygen levels of a patient and to support delivery of oxygen to the patient via the oxygen tube, and wherein the flexible ear cuff is configured to nestle between a pinna of an ear of the patient and a head of the patient; and a proximity sensor comprising two pieces connected by a hinge, the two pieces are configured to: surround the oxygen tube at or near the second end, determine a displacement of the oxygen tube, and issue an alert upon the determination of the displacement of the oxygen tube.

2. The device of claim 1, further comprising:

the pulse oximeter with an earlobe clamp at the first end of the flexible ear cuff.

3. The device of claim 1, wherein the two pieces are configured to close surrounding the oxygen tube and secure the proximity sensor to the oxygen tube.

4. The device of claim 1, wherein the flexible ear cuff is configured to slide over the oxygen tube.

5. The device of claim 1, wherein the flexible ear cuff is made of silicone.

6. The device of claim 1, wherein the displacement of the oxygen tube is determined based on a change in distance between the proximity sensor and the patient.

7. The device of claim 1, further comprising a wireless communication interface configured to transmit the alert to a user when the displacement exceeds a threshold.

8. The device of claim 1, wherein the oxygen tube is secured to the patient such that the proximity sensor is within a threshold proximity to skin of the patient.

9. A system for attaching an oxygen tube and a pulse oximeter to a patient, the system comprising:

a flexible ear cuff with a first end and a second end, the first end comprising a sleeve configured to receive a pulse oximeter and the second end configured to receive an oxygen tube, wherein the pulse oximeter is fitted into the sleeve, wherein the flexible ear cuff is configured to support the pulse oximeter that monitors blood oxygen levels of the patient and to support delivery of oxygen to the patient via the oxygen tube, wherein the flexible ear cuff is configured to nestle between a pinna of an ear of the patient and a head of the patient;

the pulse oximeter with an earlobe clamp at the first end of the flexible ear cuff;

the oxygen tube at the second end of the flexible ear cuff, and a proximity sensor comprising two pieces connected by a hinge, the two pieces are configured to surround the oxygen tube at or near the second end, determine a displacement of the oxygen tube, and issue an alert upon the determination of the displacement of the oxygen tube based on a change in distance between the proximity sensor and the patient.

10. The system of claim 9, wherein the proximity is configured to issue the alert when a distance between skin of the patient and the proximity sensor breaches a threshold.

11. The system of claim 9, wherein the two pieces are configured to secure the proximity sensor to the oxygen tube.

12. The system of claim 9, wherein the flexible ear cuff is configured to slide over the oxygen tube.

13. The system of claim 9, wherein the flexible ear cuff is made of silicone.

14. A method comprising:

attaching a flexible ear cuff over an oxygen tube, wherein the flexible ear cuff comprises a first end and a second end, the first end comprising a sleeve configured to receive a pulse oximeter and the second end configured to receive an oxygen tube, wherein the pulse oximeter is fitted into the sleeve, wherein the flexible ear cuff is configured to nestle between a pinna of an ear of a patient and a head of the patient, and wherein the flexible ear cuff is configured to support the pulse oximeter that monitors blood oxygen levels of the patient and to support delivery of oxygen to the patient via the oxygen tube; and attaching a proximity sensor to the oxygen tube, to determine a displacement of the oxygen tube and issue an alert upon the determination of the displacement of the oxygen tube, wherein the proximity sensor comprises two pieces connected by a hinge.

15. The method of claim 14, further comprising:

attaching the pulse oximeter, with an earlobe clamp at the first end of the flexible ear cuff, to an earlobe of the patient.

16. The method of claim 14, wherein the proximity sensor is configured to issue the alert when a distance between skin of the patient and the proximity sensor breaches a threshold.

17. The method of claim 14, wherein the two pieces are configured to secure the proximity sensor to the oxygen tube.

18. The method of claim 14, wherein the flexible ear cuff is configured to slide over the oxygen tube.

* * * * *